United States Patent
Brahma (10) Patent No.: US 9,606,092 B2
(45) Date of Patent: Mar. 28, 2017

(54) NO$_x$ SENSOR DIAGNOSIS SYSTEM AND METHOD

(71) Applicant: CUMMINS EMISSION SOLUTIONS, INC., Columbus, IN (US)

(72) Inventor: Avra Brahma, Fishers, IN (US)

(73) Assignee: Cummins Emission Solutions, Inc., Columbus, IN (US)

( * ) Notice: Subject to any disclaimer, the term of this patent is extended or adjusted under 35 U.S.C. 154(b) by 191 days.

(21) Appl. No.: 14/454,403

(22) Filed: Aug. 7, 2014

(65) Prior Publication Data

US 2016/0041137 A1     Feb. 11, 2016

(51) Int. Cl.
*F01N 3/18*          (2006.01)
*G01N 33/00*       (2006.01)
*G01M 15/10*       (2006.01)

(52) U.S. Cl.
CPC ...... *G01N 33/0006* (2013.01); *G01M 15/102* (2013.01); *F01N 3/18* (2013.01)

(58) Field of Classification Search
CPC .. F01N 2560/026; F01N 3/208; F01N 3/2066; F01N 3/035; F01N 2560/14; F01N 3/0814; F01N 2900/0416; F01N 2570/14; F01N 11/002; F01N 11/007; F01N 2250/12; F01N 2900/0408; F01N 2610/144; G01R 19/0092; G01M 15/102; G01M 15/10
See application file for complete search history.

(56) References Cited

U.S. PATENT DOCUMENTS

| | | | |
|---|---|---|---|
| 5,027,646 A | 7/1991 | Mizutani et al. |
| 5,265,416 A | 11/1993 | Hamburg et al. |
| 5,483,817 A | 1/1996 | Renard et al. |
| 5,558,752 A | 9/1996 | Wang et al. |
| 6,371,096 B1 | 4/2002 | Ohsaki et al. |
| 6,481,273 B2 | 11/2002 | Maloney |
| 6,996,499 B2 | 2/2006 | Kurokawa et al. |
| 7,021,300 B2 | 4/2006 | Maki et al. |
| 7,225,800 B2 | 6/2007 | Nakagawa et al. |
| 7,752,837 B2 | 7/2010 | Iihoshi et al. |

(Continued)

FOREIGN PATENT DOCUMENTS

WO    WO 2009098798    8/2009

OTHER PUBLICATIONS

International Search Report and Written Opinion for PCT/US2015/042470, issued Nov. 2, 2015, 9 pages.

*Primary Examiner* — Vinh Nguyen
(74) *Attorney, Agent, or Firm* — Foley & Lardner LLP (57) ABSTRACT

Systems and methods for diagnosing a sensor for an exhaust system may include perturbing an output signal from the sensor for the exhaust system. The method may further include monitoring an output signal from a controller for controlling a component affecting the exhaust system or an unperturbed output signal from the sensor and diagnosing the sensor based on the monitored output signal from the controller or the unperturbed output signal from the sensor. In another implementation, a first controller may output the output signal from the sensor to a second controller configured to have a predetermined response to output signal. The first controller receives a response from the second controller and diagnoses the sensor based on the received response.

24 Claims, 4 Drawing Sheets

(56) References Cited

U.S. PATENT DOCUMENTS

| | | |
|---|---|---|
| 7,890,310 B2 | 2/2011 | Glass et al. |
| 7,980,121 B2 | 7/2011 | Matsuoka et al. |
| 8,034,291 B2 | 10/2011 | Qi et al. |
| 8,125,228 B2 | 2/2012 | Richards et al. |
| 8,132,450 B2 | 3/2012 | Shibata et al. |
| 8,195,355 B2 | 6/2012 | Inoue |
| 2004/0118106 A1* | 6/2004 | Liang ................. F01N 3/208 60/278 |
| 2010/0083743 A1 | 4/2010 | Wehmeier et al. |
| 2010/0101214 A1 | 4/2010 | Herman et al. |
| 2010/0101215 A1 | 4/2010 | Wu et al. |
| 2011/0000290 A1* | 1/2011 | Sawada ............... F02D 41/146 73/114.75 |
| 2011/0314793 A1 | 12/2011 | Mullins et al. |
| 2012/0234077 A1 | 9/2012 | Wang et al. |
| 2012/0303206 A1 | 11/2012 | Rajagopalan et al. |
| 2014/0360166 A1* | 12/2014 | Chandrasekaran ..... F01N 11/00 60/274 |

\* cited by examiner

NO$_x$ SENSOR DIAGNOSIS SYSTEM AND METHOD

TECHNICAL FIELD

The present application relates generally to the field of sensors for an aftertreatment system. More specifically, the present application relates to diagnosing a sensor.

BACKGROUND

For internal combustion engines, such as diesel engines, nitrogen oxides (NO$_x$) compounds may be emitted in the exhaust. To reduce NO$_x$ emissions, a selective catalytic reduction (SCR) process may be implemented to convert the NO$_x$ compounds into more neutral compounds, such as diatomic nitrogen, water, or carbon dioxide, with the aid of a catalyst and a reductant. The catalyst may be included in a catalyst chamber of an exhaust system, such as that of a vehicle or power generation unit. A reductant, such as anhydrous ammonia, aqueous ammonia, or urea is typically introduced into the exhaust gas flow prior to the catalyst chamber. To introduce the reductant into the exhaust gas flow for the SCR process, an SCR system may dose or otherwise introduce the reductant through a dosing module that vaporizes or sprays the reductant into an exhaust pipe of the exhaust system upstream of the catalyst chamber.

Emissions systems for such compression-ignition (e.g., diesel) engines may monitor the release of carbon monoxide (CO), unburned hydrocarbons (UHC), diesel particulate matter (PM), such as ash and soot, and NO$_x$. To monitor the release of such compounds, various sensors may be coupled to an exhaust system of the engine at various locations. For instance, NO$_x$ sensors may be coupled to the exhaust system downstream and/or upstream of a SCR system to monitor the amount of NO$_x$ upstream and/or downstream of the SCR system.

In some systems, diagnosis of a sensor consists of comparing a sensor reported value to a known reference value and identifying any low or high biases in the reported value. For exhaust systems with NO$_x$ sensors upstream and downstream of the SCR system, the reported values between the two sensors may show large differences due to the reductive activity of the NO$_x$ reducing catalyst of the SCR system and it may not be possible to compare the two sensors against each other to obtain a diagnosis. Accordingly, in some systems, an algorithmic diagnosis is performed by estimating the value of the NO$_x$ approaching the downstream sensor using mathematical models or by operating the system in a condition where the NO$_x$ converting catalyst has reduced activity.

SUMMARY

One implementation relates to a method for diagnosing a sensor for an exhaust system. The method may include perturbing an output signal from the sensor for the exhaust system. The method may also include monitoring a control signal from a controller for controlling a component affecting the exhaust system for a characteristic. The method may further include diagnosing the sensor based on the monitored characteristic of the control signal from the controller.

In some implementations, perturbing the output signal includes perturbing a gain value or an offset value. In some implementations, the sensor is a NO$_x$ sensor. In some implementations, the characteristic of the control signal may be one of a command or a cycling frequency. In some implementations, diagnosing the sensor based on the monitored characteristic of the control signal determines the sensor is not defective responsive to the perturbed output signal if the characteristic is one of a stable response, a sine response, an expected response, or a smooth response. In some implementations, diagnosing the sensor based on the monitored characteristic of the control signal determines the sensor is defective responsive to the perturbed output signal if the characteristic is one of an unstable response, a limit cycle response, an unexpected response, or a saturated controller response.

Another implementation relates to a method for diagnosing a sensor for an exhaust system. The method may include perturbing an output signal from the sensor for the exhaust system. The method may also include monitoring the unperturbed output signal from the sensor prior to the introduced perturbation. The method may further include diagnosing the sensor based on the monitored unperturbed output signal from the sensor.

In some implementations, perturbing the output signal includes perturbing a gain value or an offset value. In some implementations, the sensor is a NO$_x$ sensor. In some implementations, diagnosing the sensor based on the monitored unperturbed output signal determines the sensor is not defective responsive to the perturbed output signal if the monitored unperturbed output signal responds in an expected direction to the perturbing of the output signal. In some implementations, diagnosing the sensor based on the monitored unperturbed output signal determines the sensor is defective responsive to the perturbed output signal if the monitored unperturbed output signal responds in a reduced expected direction to the perturbing of the output signal or in a contrary direction to the perturbing of the output signal.

Yet a further implementation relates to a system having an exhaust system including a SCR catalyst and a reductant dosing module upstream of the SCR catalyst. The system includes a sensor coupled to the exhaust system downstream of the SCR catalyst and configured to detect a condition of the exhaust system, a first controller configured to control a portion of the exhaust system responsive to an output signal from the sensor, and a second controller configured to have a predetermined design characteristic to output signals from a non-defective sensor. The first controller may be further configured to output the output signals from the sensor to the second controller, receive a response from the second controller responsive to the output signals from the sensor, and diagnose the sensor based on the received response.

In some implementations, the second controller forms a closed loop control system and diagnosing the sensor based on the received response includes analyzing a property or characteristic of the closed loop control system when the second controller is activated. In some implementations, diagnosing the sensor based on the received response includes analyzing roots of the closed loop control system when the second controller is activated. In some implementations, diagnosing the sensor based on the received response includes analyzing a gain or phase margin of the closed loop control system when the second controller is activated. In some implementations, the second controller forms a closed loop control system and the predetermined design characteristic of the closed loop control system based on the second controller may be a step response. The step response may be a function of gain of the sensor. The first controller may be further configured to determine a gain of the sensor based on the step response. In some implementations, the first controller is configured to temporarily output the output signals from the sensor to the second controller and/or perturb the output signals from the sensor.

Still a further implementation relates to an apparatus that includes a first module, a second module, and a third module. The first module is configured to perturb an output signal from a $NO_x$ sensor for an exhaust system. The second module is configured to monitor a characteristic of an output signal from a controller for controlling a component affecting the exhaust system or an unperturbed output signal from the $NO_x$ sensor. The third module is configured to diagnose the sensor based on the monitored characteristic of the output signal from the controller or the unperturbed output signal from the $NO_x$ sensor.

In some implementations, the output signal from the controller is one of a dosing amount or a dosing rate. In some implementations, perturbing the output signal is one of a gain or an offset. In some implementations, the characteristic of the output signal from the controller is one of a command or a cycling frequency.

BRIEF DESCRIPTION OF THE DRAWINGS

The details of one or more implementations are set forth in the accompanying drawings and the description below. Other features, aspects, and advantages of the disclosure will become apparent from the description, the drawings, and the claims, in which:

It will be recognized that some or all of the figures are schematic representations for purposes of illustration. The figures are provided for the purpose of illustrating one or more implementations with the explicit understanding that they will not be used to limit the scope or the meaning of the claims.

DETAILED DESCRIPTION

Following below are more detailed descriptions of various concepts related to, and implementations of, methods, apparatuses, and systems for diagnosing rationality of a sensor for an exhaust system. The various concepts introduced above and discussed in greater detail below may be implemented in any of numerous ways, as the described concepts are not limited to any particular manner of implementation. Examples of specific implementations and applications are provided primarily for illustrative purposes.

I. Overview

To effectively measure compounds that are emitted from an engine to the atmosphere from an exhaust system, various sensors are utilized to determine and/or estimate the concentration of the compound in the exhaust gas from the exhaust system. For instance, a $NO_x$ sensor downstream of a SCR system may measure the $NO_x$ emitted from the engine to the atmosphere. Similarly, a CO sensor may measure the CO emitted from the engine to the atmosphere. Other sensors may measure the concentration of other compounds or characteristics of the exhaust gas.

However, such sensors may be faulty initially and/or degrade over time and/or usage. For instance, a sensor may develop an abnormal gain for an output value from the sensor and/or an abnormal offset to the output value from the sensor. Such characteristics, gain and/or offset, of the output signal of the sensor may negatively affect an aftertreatment system of the engine. For instance, the sensor output signal of a $NO_x$ sensor may be used to determine the amount of reductant to dose upstream of a SCR catalyst, to modify an operating condition of the engine, to modify an operating condition of an EGR valve or system, to initiate or stop a regeneration process, etc. Thus, determining whether the sensor is defective or not defective can impact various aspects of an aftertreatment system and/or engine.

In some implementations, rationality diagnosis is performed to determine whether the sensor is defective or not defective. Rationality diagnosis of a sensor consists of comparing a sensor reported value to a known reference value and identifying any low or high biases in the reported value. In some systems, an algorithmic rationality diagnosis is performed by estimating the concentration of a compound in the exhaust gas approaching a downstream sensor using mathematical models or by operating the system in a condition where the concentration of a compound is sufficiently equal to a concentration of the compound measured by an upstream sensor. However, such systems may be limited by the accuracy or inaccuracy of the estimation of the concentration of a compound in the gas approaching the downstream sensor and/or operate the engine at conditions that are inefficient or wasteful.

Implementations described herein involve perturbing a characteristic of a sensor output, such as gain or offset, and monitoring an aspect of a system response to diagnose the sensor. In some implementations, an alternative control system or controller having a known response to various sensor characteristics may be activated by a first controller to be utilized for diagnostic purposes.

In an implementation, a controller may monitor a characteristic of a closed loop control system, such as a closed loop command, closed loop command cycling frequency, etc., in response to an active and intrusive perturbation of a sensor characteristic, such as gain or offset, introduced into the output of the sensor signal, such as via one or more modules. Such a controller may detect a defective sensor based on a distinct difference in the closed loop controller response to the known intrusive perturbation of the characteristic of the sensor. For instance, for a non-defective sensor, the closed loop command may be stable in response to a fixed, positive perturbation in sensor gain. In contrast, for a defective sensor with a high gain, the closed loop command may limit cycle at a frequency in response to the same perturbation.

In another implementation, a controller may monitor an unperturbed sensor output signal (e.g., the raw sensor output signal) from the sensor to determine the response to an active and intrusive perturbation to a characteristic of the sensor output signal, such as a gain or offset. Such a controller may detect a defective sensor based on a difference in the unperturbed sensor output signal responsive to the known intrusive perturbation of the characteristic of the sensor. For instance, for a non-defective sensor, the unperturbed output signal from the sensor may show a drop in the concentration of the compound detected by the sensor in response to a positive perturbation in sensor gain. In contrast, for a defective sensor with a high gain, the unperturbed output signal may indicate a lesser or absent drop or an increase in the detected concentration for an identical perturbation.

In yet another implementation, a second closed loop controller distinct from the monitoring logic and the primary controller may be utilized for diagnosing a defective sensor. The second controller may be specifically designed for such diagnosis. The second controller may be activated by a first controller and receive the output signal from the sensor being diagnosed. The second controller may be configured to have a known design characteristic to the characteristic of the output signal of the sensor being diagnosed, such as a known response to gain or offset. For instance, a controller or control system with a known root locus characteristic, gain, or phase margins to a characteristic of an output signal of a sensor, such as gain or offset, may be designed. The diagnosis may be performed by analyzing the roots of the closed loop control system or the gain and/or phase margins when the controller is enabled and for the received output signal of the sensor. In another implementation, the controller or control system may be designed and/or configured to have predetermined step response characteristics as a function of a characteristic of the output signal of the sensor, such as gain or offset. The first controller may diagnose the sensor based on the response of the second controller to the output signal of the sensor. The first controller may temporarily utilize the second controller and evaluating the response to infer the characteristic of the output signal of the sensor, such as gain or offset.

II. Overview of Aftertreatment System

Figure 1:
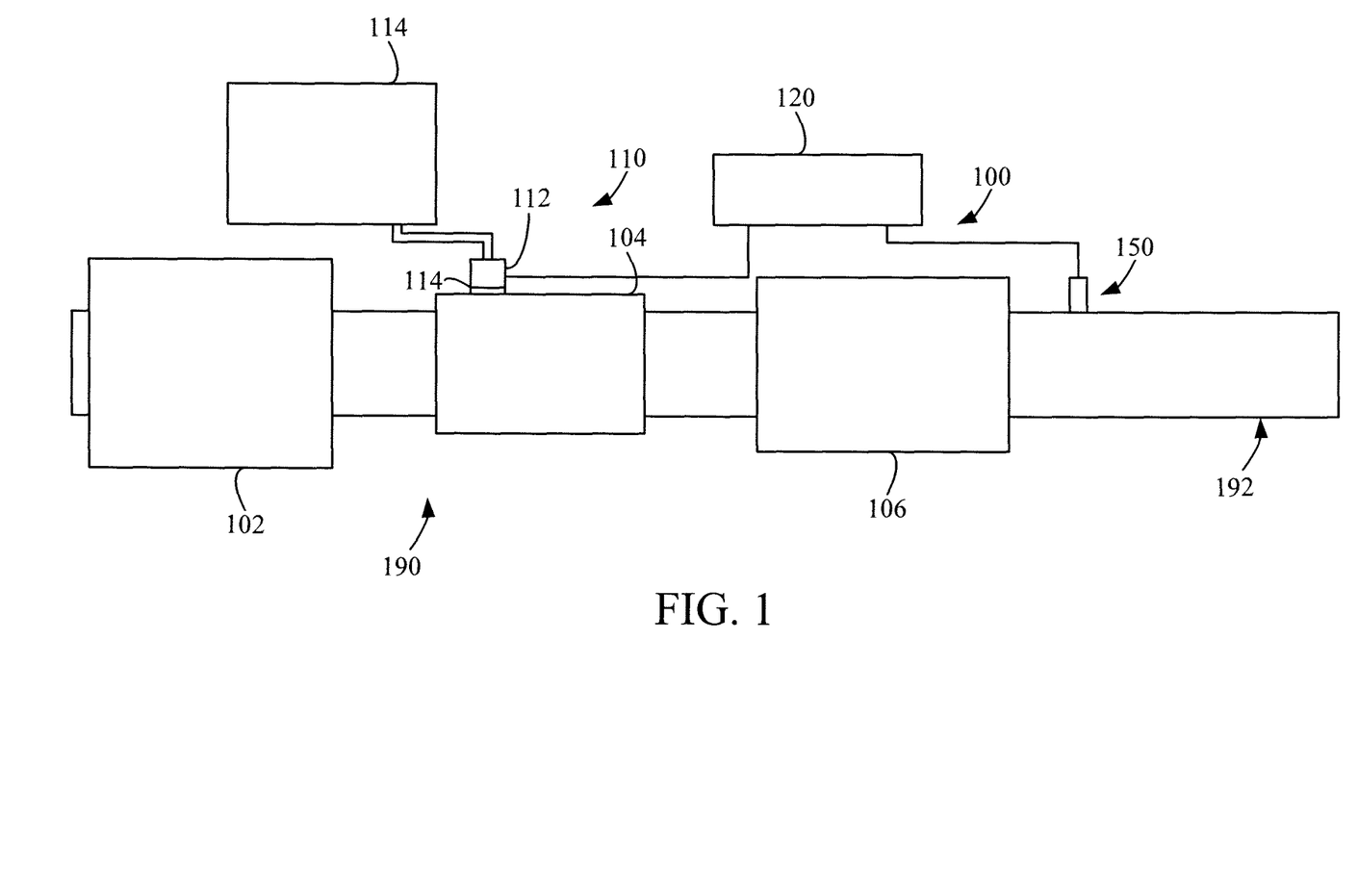
FIG. 1 is a block schematic diagram of a selective catalytic reduction system having a reductant delivery system for an exhaust system.

FIG. 1 depicts an aftertreatment system 100 having an example reductant delivery system 110 for an exhaust system 190. The aftertreatment system 100 includes a diesel particulate filter (DPF) 102, the reductant delivery system 110, a decomposition chamber or reactor 104, a SCR catalyst 106, and a sensor probe 150.

The DPF 102 is configured to remove particulate matter, such as soot, from exhaust gas flowing in the exhaust system 190. The DPF 102 includes an inlet, where the exhaust gas is received, and an outlet, where the exhaust gas exits after having particulate matter substantially filtered from the exhaust gas and/or converting the particulate matter into carbon dioxide.

The decomposition chamber 104 is configured to convert a reductant, such as urea, aqueous ammonia, or diesel exhaust fluid (DEF), into ammonia. The decomposition chamber 104 includes a reductant delivery system 110 having a dosing module 112 configured to dose the reductant into the decomposition chamber 104. In some implementations, the urea, aqueous ammonia, DEF is injected upstream of the SCR catalyst 106. The reductant droplets then undergo the processes of evaporation, thermolysis, and hydrolysis to form gaseous ammonia within the exhaust system 190. The decomposition chamber 104 includes an inlet in fluid communication with the DPF 102 to receive the exhaust gas containing NOx emissions and an outlet for the exhaust gas, NOx emissions, ammonia, and/or remaining reductant to flow to the SCR catalyst 106.

The decomposition chamber 104 includes the dosing module 112 mounted to the decomposition chamber 104 such that the dosing module 112 may dose a reductant, such as urea, aqueous ammonia, or DEF, into the exhaust gases flowing in the exhaust system 190. The dosing module 112 may include an insulator 114 interposed between a portion of the dosing module 112 and the portion of the decomposition chamber 104 to which the dosing module 112 is mounted. The dosing module 112 is fluidly coupled to one or more reductant sources 116. In some implementations, a pump (not shown) may be used to pressurize the reductant source 116 for delivery to the dosing module 112.

The dosing module 112 is also electrically or communicatively coupled to a controller 120. The controller 120 is configured to control the dosing module 112 to dose reductant into the decomposition chamber 104. The controller 120 may include a microprocessor, an application-specific integrated circuit (ASIC), a field-programmable gate array (FPGA), etc., or combinations thereof. The controller 120 may include memory which may include, but is not limited to, electronic, optical, magnetic, or any other storage or transmission device capable of providing a processor, ASIC, FPGA, etc. with program instructions. The memory may include a memory chip, Electrically Erasable Programmable Read-Only Memory (EEPROM), erasable programmable read only memory (EPROM), flash memory, or any other suitable memory from which the controller 120 can read instructions. The instructions may include code from any suitable programming language. The controller 120 may be configured to control other components of the exhaust system 190 and/or an engine or other components associated with the exhaust system 190. For instance, the controller 120 may be configured to modify an operating condition of the engine, to modify an operating condition of an EGR valve or system, to initiate or stop a regeneration process, etc.

The SCR catalyst 106 is configured to assist in the reduction of NOx emissions by accelerating a NOx reduction process between the ammonia and the NOx of the exhaust gas into diatomic nitrogen, water, and/or carbon dioxide. The SCR catalyst 106 includes inlet in fluid communication with the decomposition chamber 104 from which exhaust gas and reductant is received and an outlet in fluid communication with an end 192 of the exhaust system 190.

The exhaust system 190 may further include a diesel oxidation catalyst (DOC) in fluid communication with the exhaust system 190 (e.g., downstream of the SCR catalyst 106 or upstream of the DPF 102) to oxidize hydrocarbons and carbon monoxide in the exhaust gas.

The sensor probe 150 may be coupled to the exhaust system 190 to detect a condition of the exhaust gas flowing through the exhaust system 190. In some implementations, the sensor probe 150 may have a portion disposed within the exhaust system 190, such as a tip of the sensor probe 150 may extend into a portion of the exhaust system 190. In other implementations, the sensor probe 150 may receive exhaust gas through another conduit, such as a sample pipe extending from the exhaust system 190. While the sensor probe 150 is depicted as positioned downstream of the SCR catalyst 106, it should be understood that the sensor probe 150 may be positioned at any other position of the exhaust system 190, including upstream of the DPF 102, within the DPF 102, between the DPF 102 and the decomposition chamber 104, within the decomposition chamber 104, between the decomposition chamber 104 and the SCR catalyst 106, within the SCR catalyst 106, or downstream of the SCR catalyst 106. In addition, two or more sensor probes 150 may be utilized for detecting a condition of the exhaust gas, such as two, three, four, five, or size sensor probes 150 with a sensor probe 150 located at any of the foregoing positions of the exhaust system 190. In some implementations a first sensor probe 150 may be upstream of the SCR catalyst 106 and a second sensor probe 150 may be downstream of the SCR catalyst 106. In other implementations, the first sensor probe 150 may be upstream of the decomposition chamber 104 and the second sensor probe 150 may be downstream of the SCR catalyst 106. In still other implementations, the first sensor probe 150 may be upstream of the DPF 102, and the sensor probe 150 may be downstream of the SCR catalyst 106. Still further configurations for the sensor probes 150 may be implemented.

In some implementations, the sensor probe 150 is configured to detect a concentration of a compound in the exhaust gas flowing through the exhaust system 190 and to output an output signal to the controller 120. The controller 120 may be configured to use the output signal of from the sensor to modify and/or output a control signal to a component of the exhaust system 190, an engine, and/or another component. For instance, the controller 120 may receive the output signal from the sensor 150 and modify the control signal for the dosing module 112 to increase, decrease, and/or maintain an amount of reductant dosed into the exhaust system 190.

III. Implementations for Diagnosing Sensors

Figure 2:
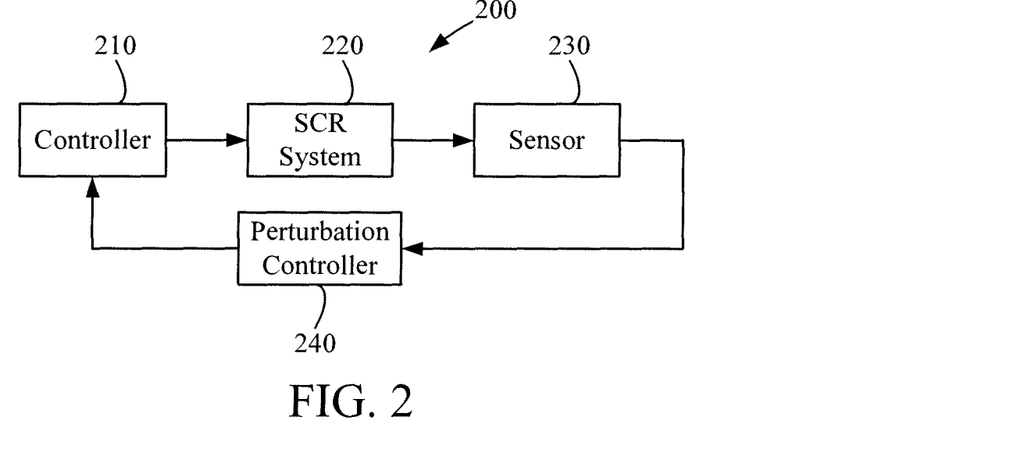
FIG. 2 is a block schematic diagram of an implementation of a system for diagnosing rationality of a sensor.

FIG. 2 depicts an implementation of a system 200 for diagnosing a sensor 230 by introducing a perturbation to a characteristic of an output signal from the sensor 230. In normal operation, a controller 210 receives an output signal from a sensor 230 and modifies a control signal for a component of an SCR system 220, an engine, or other component responsive to the value of the output signal. The controller 210 may be a microprocessor, an application-specific integrated circuit (ASIC), a field-programmable gate array (FPGA), etc., or combinations thereof. The controller 210 may include memory which may include, but is not limited to, electronic, optical, magnetic, or any other storage or transmission device capable of providing a processor, ASIC, FPGA, etc. with program instructions. The memory may include a memory chip, Electrically Erasable Programmable Read-Only Memory (EEPROM), erasable programmable read only memory (EPROM), flash memory, or any other suitable memory from which the controller 210 can read instructions. The instructions may include code from any suitable programming language.

When the sensor 230 is operating normally (i.e., is not defective), the control signal output from the controller 210 is modified to an appropriate value to result in a desired change to the system 200 based on the value of the output signal of the sensor 230. That is, for instance, if a $NO_x$ sensor 230 determines that a level of $NO_x$ output from the SCR system 220 is 20 parts per million (ppm) and a desired level of $NO_x$ output from the SCR system 220 is 5 ppm, then the controller 210 is configured to modify a control signal, such as a control signal for a dosing module, to effect a change to the operation of the system 200 to approach and/or result in the desired level of $NO_x$ output by the SCR system 220.

However, in some implementations, the sensor 230 may be defective or degraded such that the output signal from the sensor 230 is not representative of the true value measured. That is, the sensor 230 may have a gain or offset affecting the output signal of the sensor 230 such that the output signal is different than the true value. For instance, degradation of a $NO_x$ sensing material may result in a gain affecting the output signal. In other instances, an offset may be introduced into the output signal, such as a crack or leak in a chamber of a $NO_x$ sensor 230, which may permit a portion of the $NO_x$ sample to escape from the $NO_x$ sensor 230 and/or introduction of excess atmosphere into the sample chamber, thereby offsetting the measured value of $NO_x$.

The system 200 may include a component that introduces a perturbation into the output signal from the sensor 230. The perturbation may be introduced via a perturbation controller 240 receiving the output signal of the sensor 230 and introducing a known gain and/or offset to the output signal from the sensor 230. The perturbation controller 240 can then output the perturbed output signal to the controller 210 of the system 200. In some implementations, the perturbation controller 240 introducing the perturbation may be a computer executing one or more modules to modify the output signal from the sensor 230, such as part of an analog to digital (A/D) converter. In other implementations, the perturbation controller 240 may be a microprocessor, an application-specific integrated circuit (ASIC), a field-programmable gate array (FPGA), etc., or combinations thereof. The perturbation controller 240 may include memory which may include, but is not limited to, electronic, optical, magnetic, or any other storage or transmission device capable of providing a processor, ASIC, FPGA, etc. with program instructions. The memory may include a memory chip, Electrically Erasable Programmable Read-Only Memory (EEPROM), erasable programmable read only memory (EPROM), flash memory, or any other suitable memory from which the perturbation controller 240 can read instructions. The instructions may include code from any suitable programming language.

In some implementations, the perturbation controller 240 may output the known gain and/or offset to the controller 210 with the perturbed output signal. The controller 210 may monitor a characteristic of a control signal output from the controller 210 for controlling a component affecting the exhaust system, such as a component of the SCR system 220, a component of the engine, and/or another component. The controller 210 may diagnose the sensor based on the monitored characteristic of the control signal from the controller 210. That is, the controller 210 may evaluate a characteristic of the closed loop control system 200, such as a closed loop command control signal, a closed loop command cycling frequency of the control signal, etc., in response to the known, active and intrusive perturbation from the perturbation controller 240 to a characteristic of the output signal of the sensor 230, such as gain or offset. The controller 210 may diagnose the sensor 230 as not defective if the characteristic of the control signal responds in an expected direction to the perturbing of the output signal, such as one of a stable response, a sine response, or a smooth response in response to the known perturbation. For instance, if a known gain is introduced for a non-defective $NO_x$ sensor, the controller 210 may output a control signal, such as a command, to modify the dosing rate or amount in response to the perturbed output signal from the sensor 230. The increased dosing rate or amount may further reduce the amount of $NO_x$ measured by the sensor 230 and output in the output signal. The system 200 may settle to a steady state based on the known perturbed gain to the output signal. The system 200 may perform similarly based on an introduced known offset to the output signal of the sensor 230.

The controller 210 may determine the sensor is defective responsive to the perturbed output signal if the characteristic responds in a reduced expected direction to the perturbing of the output signal or in a contrary direction to the perturbing of the output signal, such as one of an unstable response, a limit cycle response, or a saturated controller response. For instance, if a known gain is introduced for a defective $NO_x$ sensor having a high gain, the controller 210 may output a control signal, such as a command, to modify the dosing rate or amount in response to the perturbed output signal from the sensor 230. The increased dosing rate or amount may increase the amount of $NO_x$ measured by the sensor 230 and output in the output signal due to additional $NH_3$ slippage from the catalyst. The command signal output from the controller 210 for the system 200 may limit cycle at a frequency in response to the gain perturbation. That is, the control signal from the controller 210 may oscillate between two or more values based on the error introduced by the gain of the defective $NO_x$ sensor 230. Based on this limit cycle, the controller 210 may determine the $NO_x$ sensor 230 is defective. The system 200 may perform similarly based on an introduced known offset to the output signal of the sensor 230.

In some implementations, the perturbation controller 240 may monitor the output control signal of the controller 210 and diagnose the sensor based on the monitored characteristic of the control signal from the controller 210. In still other implementations, the controller 210 and the perturbation controller 240 may be combined in a single controller.

Figure 3:
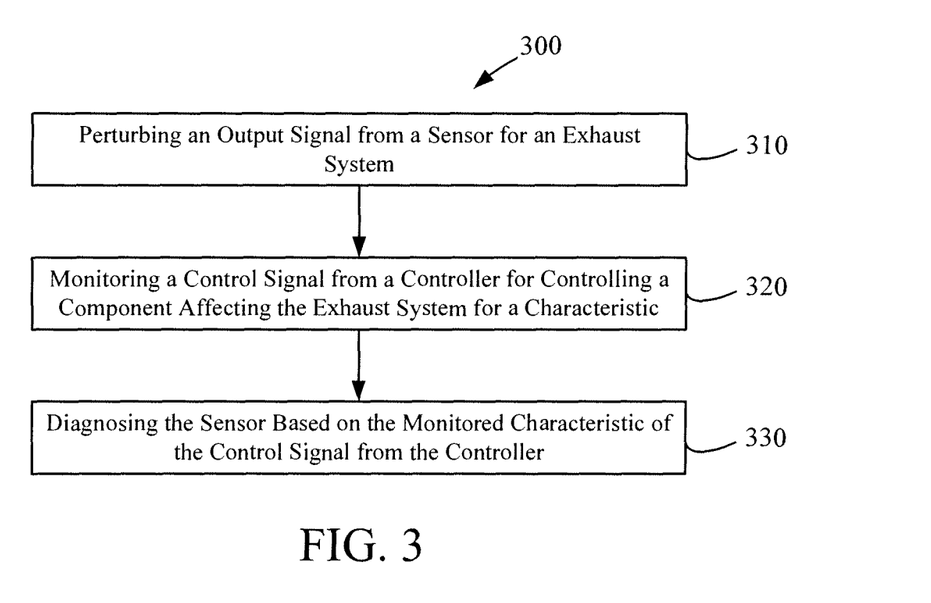
FIG. 3 is a process diagram for an implementation of a process of diagnosing rationality of the sensor for the system of FIG. 2.

FIG. 3 depicts an example process 300 that may be implemented by the system 200 for determining sensor rationality. The process 300 includes perturbing an output signal from a sensor for an exhaust system (block 310). The perturbation may be a known gain, offset, or gain and offset introduced to the output signal from the sensor of the exhaust system. In some implementations, the perturbation may be introduced using a controller and/or computer receiving the output signal from the sensor and outputting a perturbed output signal to a controller for controlling one or more components affecting the exhaust system. In some implementations the sensor is a $NO_x$ sensor. In other implementations the sensor is a CO sensor. In still other implementations the sensor is a gas sensor.

The process 300 includes monitoring a control signal from a controller for controlling a component affecting the exhaust system for a characteristic (block 320). The characteristic of the monitored control signal may be a command or a cycling frequency. In some implementations, the monitored control signal is a dosing rate. In other implementations, the monitored control signal is a dosing amount. In further implementations, the monitored control signal is an EGR valve position value.

The process 300 further includes diagnosing the sensor based on the monitored characteristic of the control signal from the controller (block 330). Diagnosing the sensor based on the monitored characteristic of the control signal may determine that the sensor is not defective responsive to the perturbed output signal if the characteristic is one of a stable response, a sine response, an expected response, or a smooth response. For instance, a system having a controller and the sensor may settle to a steady state based on a known perturbed gain or offset introduced to the output signal from the sensor. Diagnosing the sensor based on the monitored characteristic of the control signal may determine the sensor is defective responsive to the perturbed output signal if the characteristic is one of an unstable response, a limit cycle response, an unexpected response, or a saturated controller response. For instance, a system having a controller and the sensor may limit cycle based on a known perturbed gain or offset introduced to the output signal from the sensor. In some implementations, the process 300 may further include outputting a state of the sensor to another component, such as activating a warning light, outputting an error code, etc.

Referring back to FIG. 2, in some implementations, the controller 210 may monitor the unperturbed output signal from the sensor 230. The controller 210 may diagnose the sensor based on the monitored unperturbed output signal from the sensor 230. That is, the controller 210 may evaluate the change in the unperturbed output signal of the sensor 230 responsive to the known, active and intrusive perturbation from the perturbation controller 240 to a characteristic of the output signal of the sensor 230, such as gain or offset. The controller 210 may determine the sensor 230 is not defective if the change in the output signal of the sensor 230 corresponds to the known perturbation. For instance, if a known gain is introduced for a non-defective $NO_x$ sensor, the controller 210 may output a control signal, such as a command, to modify the dosing rate or amount in response to the perturbed output signal from the sensor 230. The increased dosing rate or amount may further reduce the amount of $NO_x$ measured by the sensor 230 and output in the monitored unperturbed output signal. For a non-defective sensor 230, the monitored unperturbed output signal should decrease based on the known perturbation. The system 200 may perform similarly based on an introduced known offset to the output signal of the sensor 230.

The controller 210 may determine the sensor is defective if the change in the output signal of the sensor 230 does not correspond to the known perturbation. For instance, if a known gain is introduced for a defective $NO_x$ sensor having a high gain, the controller 210 may output a control signal, such as a command, to modify the dosing rate or amount in response to the perturbed output signal from the sensor 230. The increased dosing rate or amount may increase the amount of $NO_x$ measured by the sensor 230 and output in the monitored unperturbed output signal due to additional $NH_3$ slippage from the catalyst or the amount of $NO_x$ measured by the sensor 230 may not change at all. Based on the change in the output signal of the sensor 230, the controller 210 may determine the $NO_x$ sensor 230 is defective. The system 200 may perform similarly based on an introduced known offset to the output signal of the sensor 230.

In some implementations, the perturbation controller 240 may monitor the unperturbed output signal of the sensor 230 and diagnose the sensor based on the unperturbed output signal from the sensor 230. In still other implementations, the controller 210 and the perturbation controller 240 may be combined in a single controller.

Figure 4:
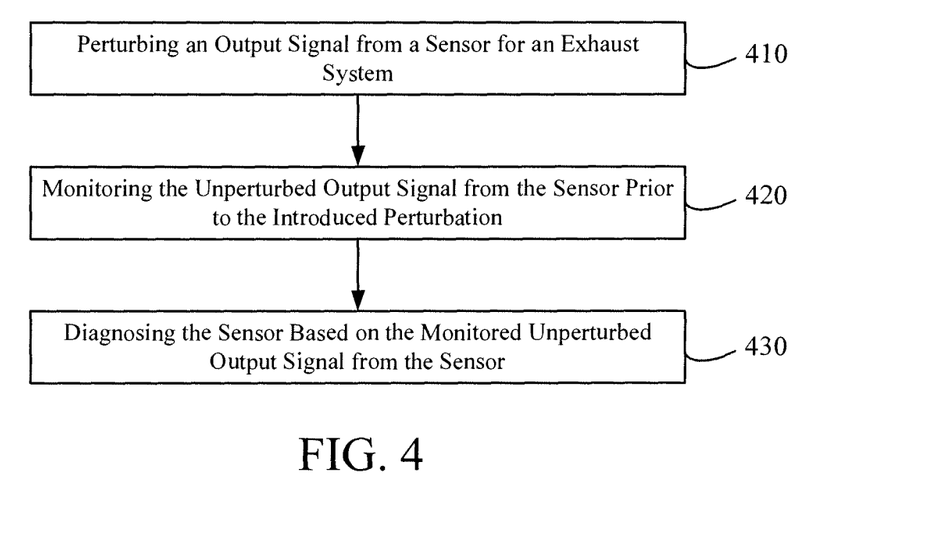
FIG. 4 is a process diagram for another implementation of a process of diagnosing rationality of the sensor for the system of FIG. 2.

FIG. 4 depicts an example process 400 that may be implemented by the system 200 for diagnosing the sensor. The process 400 includes perturbing an output signal from a sensor for an exhaust system (block 410). The perturbation may be a known gain, offset, or gain and offset introduced to the output signal from the sensor of the exhaust system. In some implementations, the perturbation may be introduced using a controller and/or computer receiving the output signal from the sensor and outputting a perturbed output signal to a controller for controlling one or more components affecting the exhaust system. In some implementations the sensor is a $NO_x$ sensor. In other implementations the sensor is a CO sensor. In still other implementations the sensor is a gas sensor.

The process 400 includes monitoring the unperturbed output signal from the sensor prior to the introduced perturbation (block 420). The process 400 further includes diagnosing the sensor based on the monitored unperturbed output signal from the sensor (block 430). Diagnosing the sensor based on the monitored unperturbed output signal may determine that the sensor is not defective responsive to the perturbed output signal if the monitored unperturbed output signal is one of a stable response, a sine response, an expected response, or a smooth response. For instance, if the monitored output signal is proportional to an introduced gain perturbation then the sensor may not be defective. Diagnosing the sensor based on the monitored unperturbed output signal may also determine that the sensor is not defective if the monitored output signal corresponds to an introduced offset perturbation. Diagnosing the sensor based on the monitored unperturbed output signal may determine the sensor is defective responsive to the perturbed output signal if the monitored unperturbed output signal is one of an unstable response, a limit cycle response, an unexpected response, or a saturated controller response. For instance, if the monitored output signal is not proportional to an introduced gain perturbation then the sensor may be defective. Diagnosing the sensor based on the monitored unperturbed output signal may also determine that the sensor is defective if the monitored output signal does not correspond to an introduced offset perturbation. In some implementations, the process 400 may further include outputting a state of the sensor to another component, such as activating a warning light, outputting an error code, etc.

Figure 5:
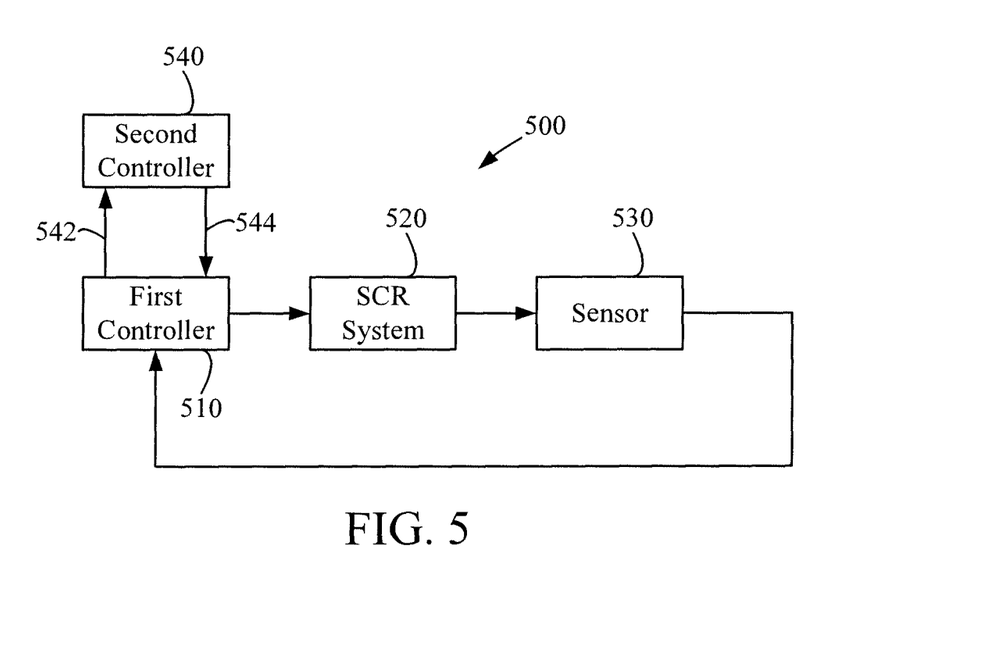
FIG. 5 is a block schematic diagram of yet another implementation of a system for diagnosing rationality of a sensor.

FIG. 5 depicts an implementation of a system 500 for diagnosing a sensor 530 by using a second controller 540 having a known response based on an output signal from the sensor 530. In normal operation, a first controller 510 receives an output signal from a sensor 530 and modifies a control signal for a component of an SCR system 520, an engine, or other component responsive to the value of the output signal. The first controller 510 may be a microprocessor, an application-specific integrated circuit (ASIC), a field-programmable gate array (FPGA), etc., or combinations thereof. The first controller 510 may include memory which may include, but is not limited to, electronic, optical, magnetic, or any other storage or transmission device capable of providing a processor, ASIC, FPGA, etc. with program instructions. The memory may include a memory chip, Electrically Erasable Programmable Read-Only Memory (EEPROM), erasable programmable read only memory (EPROM), flash memory, or any other suitable memory from which the first controller 510 can read instructions. The instructions may include code from any suitable programming language.

When the sensor 530 is operating normally (i.e., is not defective), the control signal output from the first controller 510 is modified to an appropriate value to result in a desired change to the system 500 based on the value of the output signal of the sensor 530. That is, for instance, if a $NO_x$ sensor 530 determines that a level of $NO_x$ output from the SCR system 520 is 20 parts per million (ppm) and a desired level of $NO_x$ output from the SCR system 520 is 5 ppm, then the first controller 510 is configured to modify a control signal, such as a control signal for a dosing module, to effect a change to the operation of the system 500 to approach and/or result in the desired level of $NO_x$ output by the SCR system 520.

However, in some implementations, the sensor 530 may be defective or degraded such that the output signal from the sensor 530 is not representative of the true value measured. That is, the sensor 530 may have a gain or offset affecting the output signal of the sensor 530 such that the output signal is different than the true value. For instance, degradation of a $NO_x$ sensing material may result in a gain affecting the output signal. In other instances, an offset may be introduced into the output signal, such as a crack or leak in a chamber of a $NO_x$ sensor 530, which may permit a portion of the $NO_x$ sample to escape from the $NO_x$ sensor 530 and/or introduction of excess atmosphere into the sample chamber, thereby offsetting the measured value of $NO_x$.

The system 500 may include a second controller 540 having a known response 544 based on a received input signal 542 for the output signal from the sensor 530. In some implementations, the second controller 540 may be a microprocessor, an application-specific integrated circuit (ASIC), a field-programmable gate array (FPGA), etc., or combinations thereof. The second controller 540 may include memory which may include, but is not limited to, electronic, optical, magnetic, or any other storage or transmission device capable of providing a processor, ASIC, FPGA, etc. with program instructions. The memory may include a memory chip, Electrically Erasable Programmable Read-Only Memory (EEPROM), erasable programmable read only memory (EPROM), flash memory, or any other suitable memory from which the second controller 540 can read instructions. The instructions may include code from any suitable programming language. In some implementations, the first controller 510 and the second controller 540 may be part of a single controller and may be separate modules or circuits.

In some implementations, the second controller 540 may be configured to output a known design characteristic based on a characteristic of the output signal from the sensor 530 being diagnosed, such as a characteristic of gain or offset. For instance, the second controller 540 may have known root locus characteristics, gain, and/or phase margin to gain values of the output signal from the sensor 530. The first controller 510 may activate the second controller 540 and transmit 542 the outputted signal from the sensor 530 to the second controller 540. The second controller 540 may then output a response based on the received output signal for the sensor 530 to the first controller 510. The first controller 510 may diagnose the sensor 530 by analyzing the roots of the closed loop control system when the second controller 540 is enabled. That is, the second controller 540 may form a closed loop control system and the first controller 510 may determine sensor rationality by analyzing the roots of the closed loop control system when the second controller 540 is activated.

In another implementation, the second controller 540 may be configured to output a known step response based on a characteristic of the received output signals for the sensor 530, such as a characteristic of gain or offset. For instance, the second controller 540 may have known step response characteristics as a function of gain for an output signal for the sensor 530. The first controller 510 may activate the second controller 540 and transmit 542 the outputted signal from the sensor 530 to the second controller 540. The first controller 510 receives the response 544 from the second controller 540 and uses the response 544 to diagnose the sensor 530. In some implementations, the first controller 510 may infer a gain for the sensor 530 based on the response 544 from the second controller 540.

In some implementations the first controller 510 may be configured to temporarily activate the second controller 540 and output the output signal from the sensor 530 to the second controller 540.

Figure 6:
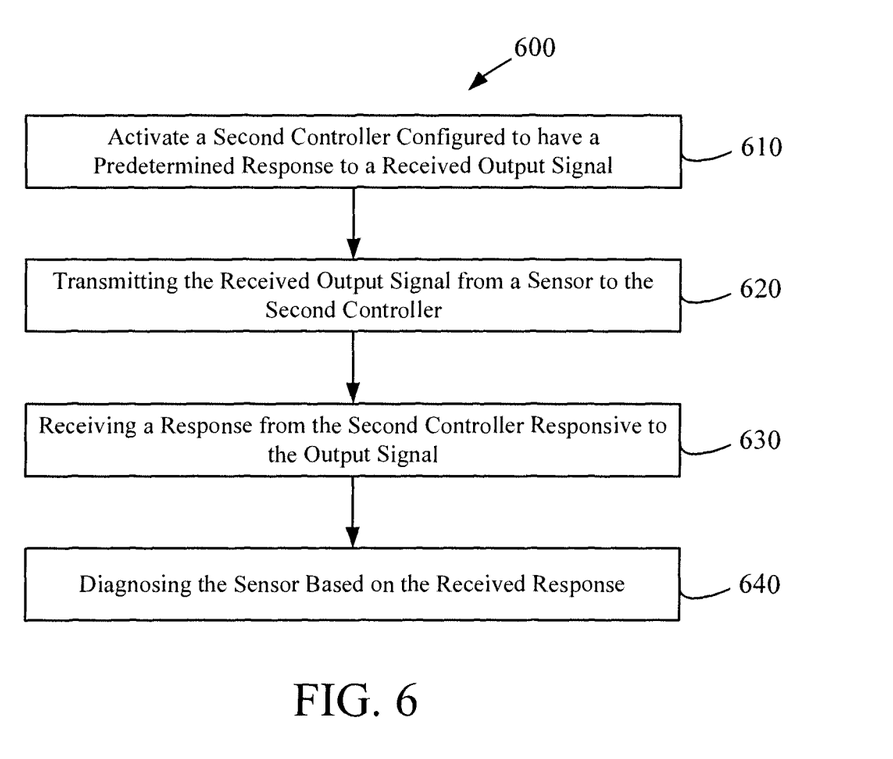
FIG. 6 is a process diagram for a process of diagnosing rationality of the sensor for the system of FIG. 5.

FIG. 6 depicts an example process 600 that may be implemented by the system 500 for diagnosing a sensor. The process 600 includes activating a second controller configured to have a predetermined response to a received output signal (block 610). In some implementations, the second controller may be activated by a separate first controller. In other implementations, the second controller may be a separate module or circuit of a single controller such that activation of the second controller may be effected by transmitting the output signal to the module or circuit. The process 600 includes transmitting the received output signal from a sensor to the second controller (block 620). In some implementations the sensor is a $NO_x$ sensor. In other implementations the sensor is a CO sensor. In still other implementations the sensor is a gas sensor.

The process 600 includes receiving a response from the second controller responsive to the output signal (block 630). In some implementations, the second controller may be configured to output a known response based on a characteristic of the output signal from the sensor being diagnosed, such as a characteristic of gain or offset. For instance, the second controller may have known root locus responses to gain values of the output signal from the sensor. The second controller may output a response based on the received output signal for the sensor to a first controller. In other implementations, the second controller may be configured to output a known step response based on a characteristic of the received output signals for the sensor, such as a characteristic of gain or offset. For instance, the second controller may have known step response characteristics as a function of gain for an output signal for the sensor. The second controller may output a response based on the received output signal for the sensor to a first controller.

The process 600 includes diagnosing the sensor based on the received response (block 640). In some implementations, the second controller may form a closed loop control system and the first controller may diagnose the sensor by analyzing the roots of the closed loop control system when the second controller is activated. In other implementations, the first controller may use the response from the second controller to diagnose the sensor, such as by inferring a gain for the sensor based on the response from the second controller configured to have known step response characteristics as a function of gain for an output signal for the sensor. In some implementations, the process 600 may further include outputting a state of the sensor to another component, such as activating a warning light, outputting an error code, etc.

In certain implementations, the systems or processes described herein can include a controller structured to perform certain operations perform the functions described herein. In certain implementations, the controller forms a portion of a processing subsystem including one or more computing devices having memory, processing, and communication hardware. The controller may be a single device or a distributed device, and the functions of the controller may be performed by hardware and/or as computer instructions on a non-transient computer readable storage medium.

In certain implementations, the controller includes one or more modules structured to functionally execute the operations of the controllers described in reference to FIGS. 2-6. The description herein including modules emphasizes the structural independence of the aspects of the controller, and illustrates one grouping of operations and responsibilities of the controller. Other groupings that execute similar overall operations are understood within the scope of the present application. Modules may be implemented in hardware and/or as computer instructions on a non-transient computer readable storage medium, and modules may be distributed across various hardware or computer based components. More specific descriptions of certain embodiments of controller operations are included in the section referencing FIGS. 2-6.

Example and non-limiting module implementation elements include sensors providing any value determined herein, sensors providing any value that is a precursor to a value determined herein, datalink and/or network hardware including communication chips, oscillating crystals, communication links, cables, twisted pair wiring, coaxial wiring, shielded wiring, transmitters, receivers, and/or transceivers, logic circuits, hard-wired logic circuits, reconfigurable logic circuits in a particular non-transient state configured according to the module specification, any actuator including at least an electrical, hydraulic, or pneumatic actuator, a solenoid, an op-amp, analog control elements (springs, filters, integrators, adders, dividers, gain elements), and/or digital control elements.

The term "controller" encompasses all kinds of apparatus, devices, and machines for processing data, including by way of example a programmable processor, a computer, a system on a chip, or multiple ones, a portion of a programmed processor, or combinations of the foregoing. The apparatus can include special purpose logic circuitry, e.g., an FPGA or an ASIC. The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as distributed computing and grid computing infrastructures.

While this specification contains many specific implementation details, these should not be construed as limitations on the scope of what may be claimed, but rather as descriptions of features specific to particular implementations. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

As utilized herein, the term "substantially" and any similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided unless otherwise noted. Accordingly, these terms should be interpreted as indicating that insubstantial or inconsequential modifications or alterations of the subject matter described and claimed are considered to be within the scope of the invention as recited in the appended claims. Additionally, it is noted that limitations in the claims should not be interpreted as constituting "means plus function" limitations under the United States patent laws in the event that the term "means" is not used therein.

The terms "coupled," "connected," and the like as used herein mean the joining of two components directly or indirectly to one another. Such joining may be stationary (e.g., permanent) or moveable (e.g., removable or releasable). Such joining may be achieved with the two components or the two components and any additional intermediate components being integrally formed as a single unitary body with one another or with the two components or the two components and any additional intermediate components being attached to one another.

It is important to note that the construction and arrangement of the system shown in the various exemplary implementations is illustrative only and not restrictive in character. All changes and modifications that come within the spirit and/or scope of the described implementations are desired to be protected. It should be understood that some features may not be necessary and implementations lacking the various features may be contemplated as within the scope of the application, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

What is claimed is:

1. A method for diagnosing a sensor for an exhaust system comprising:
    perturbing an output signal from the sensor for the exhaust system that is communicated to a controller;
    monitoring a control signal from the controller for controlling a component affecting the exhaust system for a characteristic; and
    diagnosing the sensor based on the monitored characteristic of the control signal from the controller, wherein the sensor is diagnosed as not defective responsive to the perturbed output signal if the characteristic settles to a steady state in response to the perturbation to the output signal, and wherein the sensor is diagnosed as defective responsive to the perturbed output signal if the characteristic results in limit cycling at a frequency in response to the perturbation to the output signal.

2. The method of claim 1, wherein perturbing the output signal comprises perturbing a gain value.

3. The method of claim 1, wherein perturbing the output signal comprises perturbing an offset value.

4. The method of claim 1, wherein the sensor is a $NO_x$ sensor.

5. The method of claim 1, wherein the characteristic of the control signal is one of a command or a cycling frequency.

6. A method for diagnosing a sensor for an exhaust system comprising:
    perturbing an output signal from the sensor for the exhaust system that is communicated to a controller;
    monitoring, by the controller, the unperturbed output signal from the sensor prior to the introduced perturbation; and
    diagnosing the sensor based on the monitored unperturbed output signal from the sensor based on a perturbation introduced to the perturbed output signal, wherein the sensor is diagnosed as not defective responsive to the unperturbed output signal being proportional to the perturbation introduced to the output signal, and wherein the sensor is diagnosed as defective responsive to the unperturbed output signal not being proportional to the perturbation introduced to the output signal.

7. The method of claim 6, wherein perturbing the output signal comprises perturbing a gain value.

8. The method of claim 6, wherein perturbing the output signal comprises perturbing an offset value.

9. The method of claim 6, wherein the sensor is a $NO_x$ sensor.

10. The method of claim 6, wherein diagnosing the sensor based on the monitored unperturbed output signal of the sensor determines the sensor is not defective responsive to the perturbed output signal if the monitored unperturbed output signal responds in an expected direction to the perturbing of the output signal.

11. The method of claim 6, wherein diagnosing the sensor based on the monitored unperturbed output signal of the sensor determines the sensor is defective responsive to the perturbed output signal if the monitored unperturbed output signal responds in a reduced expected direction to the perturbing of the output signal or in a contrary direction to the perturbing of the output signal.

12. A system, comprising:
    an exhaust system comprising a SCR catalyst and a reductant dosing module upstream of the SCR catalyst, the reductant dosing module configured to dose reductant into the exhaust system;
    a sensor coupled to the exhaust system downstream of the SCR catalyst, the sensor configured to detect a condition of the exhaust system;
    a first controller configured to control a portion of the exhaust system responsive to an output signal from the sensor; and
    a second controller configured to have a predetermined design characteristic to output signals from a non-defective sensor;
    the first controller further configured to selectively activate the second controller, output the output signals from the sensor to the second controller, receive a response from the second controller responsive to the output signals from the sensor, and diagnose the sensor based on the received response.

13. The system of claim 12, wherein the second controller forms a closed loop control system and diagnosing the sensor based on the received response comprises analyzing a property or a characteristic of the closed loop control system when the second controller is activated.

14. The system of claim 13, wherein diagnosing the sensor based on the received response comprises analyzing roots of the closed loop control system when the second controller is activated.

15. The system of claim 13, wherein diagnosing the sensor based on the received response comprises analyzing a gain or phase margin of the closed loop control system when the second controller is activated.

16. The system of claim 12, wherein the second controller forms a closed loop control system, and wherein the predetermined design characteristic of the closed loop control system based on the second controller is a step response.

17. The system of claim 16, wherein the step response is a function of gain of the sensor.

18. The system of claim 17, wherein the first controller is further configured to determine a gain of the sensor based on the step response.

19. The system of claim 12, wherein the first controller is configured to temporarily output the output signals from the sensor to the second controller.

20. The system of claim 12, wherein the first controller is further configured to perturb the output signals from the sensor.

21. An apparatus comprising:
    a perturbation controller configured to perturb an output signal from a $NO_x$ sensor for an exhaust system; and
    a second controller configured to:
        monitor a characteristic of an output signal from the perturbation controller for controlling a component affecting the exhaust system or an unperturbed output signal from the $NO_x$ sensor, and
        diagnose the $NO_x$ sensor based on the monitored characteristic of the output signal from the perturbation controller or the unperturbed output signal from the NO$_x$ sensor, wherein the NO$_x$ sensor is diagnosed as not defective responsive to the perturbed output signal if the characteristic settles to a steady state in response to the perturbation to the output signal, and wherein the sensor is diagnosed as defective responsive to the perturbed output signal if the characteristic results in limit cycling at a frequency in response to the perturbation to the output signal.

22. The apparatus of claim 21, wherein the output signal from the perturbation controller is one of a dosing amount or a dosing rate.

23. The apparatus of claim 21, wherein perturbing the output signal is one of a gain or an offset.

24. The apparatus of claim 21, wherein the characteristic of the output signal from the perturbation controller is one of a command or a cycling frequency.

\* \* \* \* \*